United States Patent [19]
Schoedinger, III et al.

[11] Patent Number: 6,159,212
[45] Date of Patent: Dec. 12, 2000

[54] SURGICAL TOOL AND METHOD TO REDUCE VERTEBRAL DISPLACEMENT

[76] Inventors: George R. Schoedinger, III, 12639 Old Tesson Rd., Suite 115, St. Louis, Mo. 63128; Horst K. Heiles, 402 Glen Cove Dr., Chesterfield, Mo. 63017

[21] Appl. No.: 09/365,003

[22] Filed: Aug. 2, 1999

[51] Int. Cl.[7] .................................................. A61B 17/56
[52] U.S. Cl. .............................................................. 606/61
[58] Field of Search .................................. 606/61, 60, 99, 606/90, 53, 108; 600/61; 623/17

[56] References Cited

U.S. PATENT DOCUMENTS

| | | | |
|---|---|---|---|
| 4,714,469 | 12/1987 | Kenna | 623/17 |
| 4,759,769 | 7/1988 | Hedman et al. | 623/17 |
| 4,863,476 | 9/1989 | Shepperd | 623/17 |
| 5,431,658 | 7/1995 | Moskovich | 606/99 |
| 5,536,268 | 7/1996 | Griss | 606/61 |
| 5,556,431 | 9/1996 | Buttner-Janz | 623/17 |
| 5,599,279 | 2/1997 | Slotman et al. | 600/201 |
| 5,601,556 | 2/1997 | Pisharodi | 606/61 |
| 5,653,761 | 8/1997 | Pisharodi | 623/17 |
| 5,658,336 | 8/1997 | Pisharodi | 623/17 |
| 5,688,272 | 11/1997 | Montague et al. | 606/61 |
| 5,697,889 | 12/1997 | Slotman et al. | 600/204 |
| 5,697,977 | 12/1997 | Pisharodi | 623/17 |
| 5,776,134 | 7/1998 | Howland | 606/61 |
| 5,797,910 | 8/1998 | Martin | 606/61 |

Primary Examiner—Michael Buiz
Assistant Examiner—Tan-Uyen T. Ho
Attorney, Agent, or Firm—Blackwell Sanders Peper Martin

[57] ABSTRACT

A surgical tool and method for reducing vertebral displacement between two adjacent vertebrae wherein the present tool includes a posterior compression member having a foot portion associated with one end portion thereof for selectively engaging one of the adjacent vertebrae, an anterior compression member positionable over the posterior member and having a foot portion associated with one end portion thereof for selectively engaging the other of the adjacent vertebrae, a compression nut member engagable with the posterior member for tightening against the anterior compression member, and a handle member engagable with the nut member. Using an anterior or intra-abdominal surgical approach, the present tool is inserted between the adjacent displaced vertebrae such that the foot portion associated with the posterior compression member engages the posterior vertebral margin of one of the adjacent vertebrae and the foot portion associated with the anterior compression member engages the anterior vertebral margin of the other adjacent vertebrae. With the nut member and handle member properly positioned and engaged, rotation of the handle member will cause the nut member to tighten against the anterior compression member thereby causing relative movement between the two respective flange portions and thereby effecting reduction of the vertebral displacement.

19 Claims, 4 Drawing Sheets

SURGICAL TOOL AND METHOD TO REDUCE VERTEBRAL DISPLACEMENT

TECHNICAL FIELD

This invention relates generally to a surgical tool for use in back surgery and, more particularly, to a tool and method of use to reduce vertebral displacement between two adjacent vertebrae via an anterior or intra-abdominal surgical approach, the present tool being particularly useful in reducing vertebral displacement which occurs as a result of spondylolisthesis.

BACKGROUND ART

Lumbar spondylolisthesis is a condition involving misalignment of the vertebrae in the lumbar portion of the spinal column, which condition is either developmental, acquired, or traumatic in origin. This condition typically occurs because of a discontinuity between the superior and inferior articular facets of a vertebral segment in the area known as the pars interarticularis. The resulting deformity occurs because of forward displacement of the superior vertebrae with respect to the inferior vertebrae located immediately therebelow, these vertebrae being connected by an intervertebral disc. Spondylolisthesis is classified by grade with Grade IV being the most severe. In a Grade IV situation, the superior vertebral body is completely displaced forward over the inferior vertebral body. Since the spinal canal and its contents lie immediately posterior to the vertebral body, instability with or without displacement of the vertebral body can result in compression or traction forces affecting the adjacent neural elements. These forces may produce either back or leg symptoms or both.

Spondylolisthesis is more common is young athletes, particularly, gymnasts and cricketers, where the spondylolisthesis is thought to result from stress fractures of the pars interarticularis due to recurrent stresses during extension of the spine. In elderly patients spondylolisthesis can occur without a spondylolysis due to degenerative changes in the facet joints of the spine and lax ligaments, a condition typically called degenerative spondylolisthesis. Although spondylolisthesis usually presents itself as low back pain, if the forward vertebral slip or displacement is sufficiently severe, the exit foramen for the nerve roots at the level of the spondylolisthesis may become narrowed thereby leading to nerve root entrapment and radicular symptoms.

Treatment of conditions involving misalignment of the vertebrae continues to be a challenge and a wide variety of different tools, implants, and surgical techniques and/or methods for correcting a spinal deformity have been develop to address not only spondylolisthesis reduction, but other spinal and vertebral deformities including intervertebral disc herniation. See, for example, the various surgical tools and methods of use disclosed in U.S. Pat. Nos. 5,536,268; 5,599,279; 5,601,556; 5,653,761; 5,658,336; 5,697,889; 5,697,977; 5,797,910 and 5,800,550. Although the above-identified prior art discloses a wide variety of different means for either inserting a disc implant or for spreading apart adjacent vertebrae, only U.S. Pat. Nos. 5,697,977 and 5,601,556 disclose any type of tool for accomplishing a spondylolisthesis reduction. In this regard, importantly, the present surgical tool and method of use differs both structurally and operationally from all of the prior art devices including the surgical tool disclosed in U.S. Pat. Nos. 5,601,556 and 5,697,977 relating specifically to spondylolisthesis reduction. Also, importantly, none of the prior art devices permit reduction of vertebral displacement via an anterior or intra-abdominal surgical procedure.

It is therefore desirable to provide a surgical tool and method for using the same which will not only reduce vertebral displacement, but which tool and method of use will likewise improve the overall method of treatment of conditions involving misalignment of the vertebrae and which will permit surgical treatment via an anterior or intra-abdominal surgical approach.

Accordingly, the present invention is directed to overcoming one or more of the problems as set forth above.

SUMMARY OF THE INVENTION

In accordance with the teachings of the present invention, a surgical tool and method for aligning adjacent vertebrae are disclosed wherein a posterior compression member, an anterior compression member, a cylindrical compression nut, and a handle member form the present tool. The posterior compression member is a partially-threaded rod having a flattened flange or foot portion associated with one end portion thereof orientated at approximately 90° to the longitudinal axis of the rod. The opposite end of the posterior compression rod is threaded for a portion of its overall length and includes means for cooperatively engaging a handle member which is used to properly position the foot portion relative to the posteriorly displaced vertebral body.

The anterior compression member is a tubular member having a portion of its outside surface knurled. One end portion of the anterior compression member likewise terminates in a flange or foot portion which is oriented at approximately 90° to the longitudinal axis of the tubular member, this component being sized and dimensioned to slide over the posterior compression member.

A cylindrical compression nut member having opposed end portions likewise includes a knurled circumferential surface, one end portion of the nut member being sized and shaped to cooperatively receive one end portion of the handle member. The compression nut is tapped and threaded to likewise correspond to the threaded portion associated with the posterior compression member and is threadedly engagable therewith.

The handle member is tubular is shape and is sized and shaped to slide over the threaded portion of the posterior compression member. As previously indicated, one end portion of the handle member is sized and shaped to cooperatively receive the one end portion of the posterior compression member opposite its associated foot portion and, when so engaged, rotation of the handle member will cause a corresponding rotation of the posterior foot portion so as to allow a surgeon to properly position the foot portion relative to the posteriorly displaced vertebral body. The opposite end portion of the handle member is likewise sized and shaped to cooperative engage the one end portion of the compression nut. For example, the one end portion of the handle member can be milled square so as to cooperatively engage a correspondingly milled square depression associated with the compression nut. In this regard, the anterior compression member is positioned over the posterior compression member and its foot portion positioned relative to the anteriorly displaced vertebral body. When the handle member is engaged with the compression nut, rotation of the handle member will tighten the compression nut against the anterior compression member and reduction of the vertebral displacement is performed as will be hereinafter further explained.

A typical vertebral displacement reduction using the present tool can be accomplished as follows. Using an anterior or intra-abdominal surgical approach, the present tool is inserted and positioned between the adjacent, misaligned vertebrae in the following manner. The posterior compression member of the present tool is inserted into the space between the opposing vertebrae such that its foot portion engages the posterior vertebral margin of the lower vertebral body. This positioning of the posterior foot portion is accomplished by attaching the handle member to the opposite end portion of the posterior compression member and thereafter rotating such member through use of the handle member to properly position the posterior foot portion. The anterior compression member is then positioned over the posterior compression member and its foot portion is positioned over the edge of the anteriorly displaced upper vertebral body. The compression nut is then threaded onto the posterior compression member and, using the handle member, the nut is tightened against the anterior compression member, which tightening performs the reduction of the vertebral displacement. Should the posterior foot portion become mispositioned or misaligned during the reduction process, such foot portion can be repositioned by engaging the opposite end portion of the handle member to the posterior member and thereafter rotating the same to again reposition the posterior foot portion into an optimum position. Once the reduction of the vertebral displacement is achieved and confirmed, the various components of the present tool are removed in reverse order and interbody fusion of the vertebral members can be performed using any of the known standard surgical techniques. The various components of the present tool can then be cleaned and sterilized using standard techniques for reuse.

It is therefore a principal object of the present invention to provide an improved surgical tool for use in reducing vertebral displacement.

Another object is to provide a surgical tool which is easy to use and manipulate and which is particularly adaptable for spondylolisthesis reduction using an anterior or intra-abdominal surgical procedure.

Another object is to teach an improved method for performing invertebral displacement reduction.

These and other advantages and uses of the present invention will become apparent to those skilled in the art after considering the following detailed specification in conjunction with the accompanying drawings.

BRIEF DESCRIPTION OF THE DRAWINGS

For a better understanding of the present invention, reference may be made to the accompanying drawings in which.

DETAILED DESCRIPTION OF THE INVENTION

Figure 1:
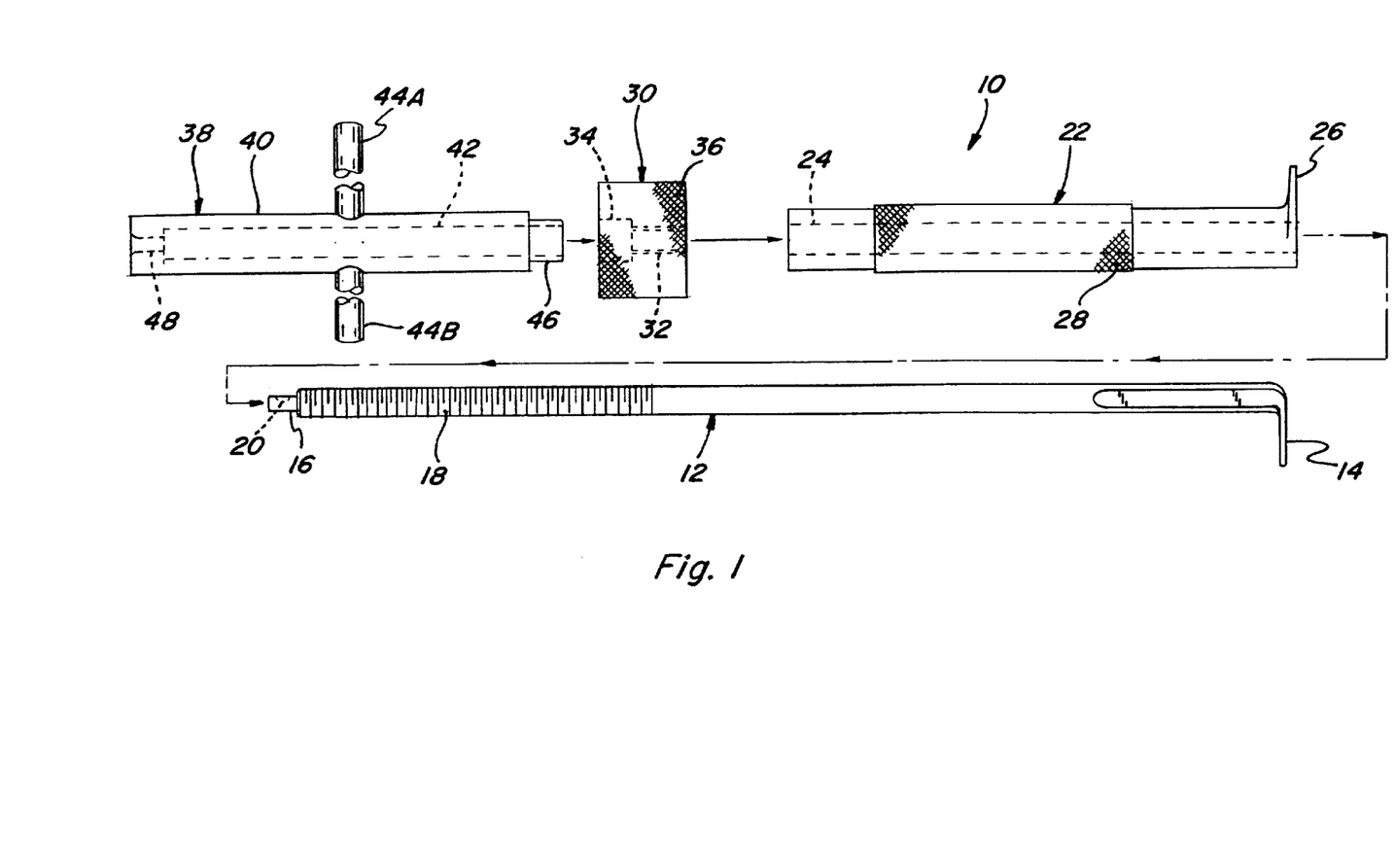
FIG. 1 is an exploded side elevational view of the various components of a surgical tool constructed according to the teachings of the present invention.
Figures 2, 3, 4, 5:
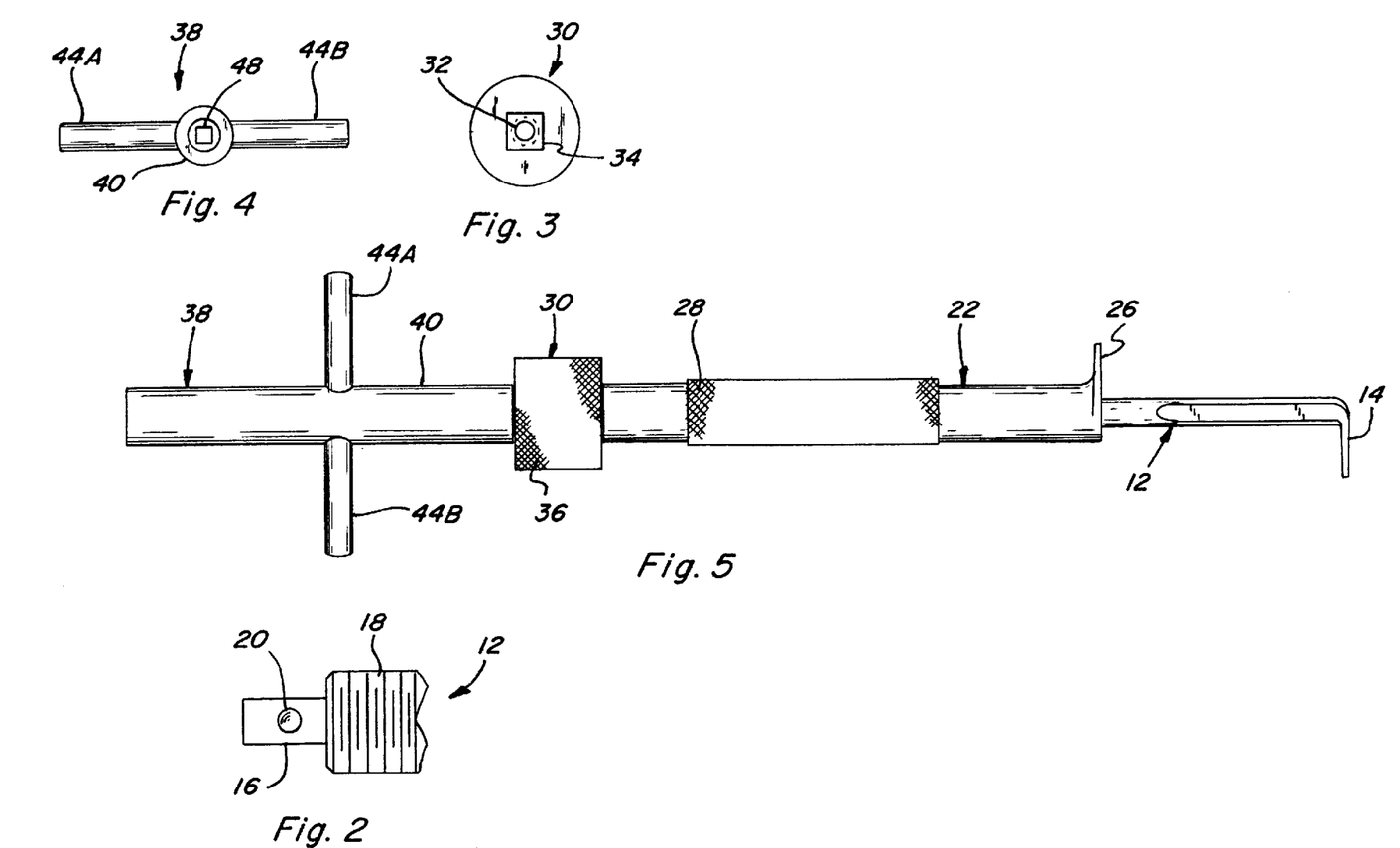
FIG. 2 is a partial side elevational view of one end portion of the present posterior compression member.
FIG. 3 is an end view of one end portion of the present compression nut.
FIG. 4 is an end view of one end portion of the present handle member.
FIG. 5 is a side elevational view of the present surgical tool shown in an assembled form for performing a vertebral displacement reduction.

Referring to the drawings more particularly by reference numbers wherein like numerals refer to like parts, number 10 in FIG. 1 identifies a surgical tool constructed according to the teachings of the present invention. The tool 10 is specifically designed for use to reduce vertebral displacement between two adjacent vertebrae and includes a posterior compression component member 12, and anterior compression component member 22, a substantially cylindrical compression nut member 30, and a handle member 38 as best illustrated in FIGS. 1 and 5. The posterior member 12 is substantially rod-like in shape and includes a flattened flange or foot portion 14 associated with one end portion thereof, the flange or foot portion 14 being substantially planar and being oriented at approximately 90° to the longitudinal axis of the rod-like member 12 so as to extend beyond the periphery of the rod member 12 on one side thereof as shown in FIGS. 1 and 5. The opposite end portion of the posterior member 12 is milled or otherwise formed into a substantially square end portion 16 as best shown in FIGS. 1 and 2 and includes a threaded portion 18 which extends along at least a portion of the overall length of the member 12 as best illustrated in FIG. 2. The squared end portion 16 likewise includes an indexing mark on one surface thereof such as the recess or indentation 20 illustrated in FIG. 1 such that a surgeon can easily locate and determine the position of the foot portion 14 associated with the opposite end portion of the member 12 based upon the position of the indentation 20 relative thereto. The squared end portion 16 is also sized and shaped so as to cooperatively receive one end portion of the handle member 38 as will be hereinafter explained. When so engaged, the handle member 38 is used to rotatably position the foot portion 14 into engagement with the posterior vertebral margin associated with the inferior vertebral body.

The anterior compression component member 22 is tubular in shape and has a passageway 24 extending therethrough from end-to-end along its entire length as shown in FIG. 1. One end portion of member 22 likewise includes a substantially planar flange or foot portion 26 which is oriented at approximately 90° to the longitudinal axis of the member 22 so as to also extend beyond the periphery of the tubular member 22 on one side thereof similar to member 12. The passageway 24 is sized and shaped so as to receive the posterior member 12 as best shown in FIG. 5 and the outer surface of the member 22 may include a knurled portion 28 for facilitating the gripping of the member 22 by a surgeon during use. The anterior member 22 is also sized and dimensioned so as to receive and slide over the posterior member 12 and, as such, the overall length of the member 22 is less than the overall length of the member 12. When the posterior member 12 is slidably position within the passageway 24, the member 22 is freely rotatable about member 12 such that the foot portion 26 can be properly positioned relative to the superior vertebral body during a surgical procedure as will be hereinafter further explained.

The present tool 10 likewise includes a cylindrical compression nut member 30 as best shown in FIGS. 1, 3 and 5. The nut member 30 includes a threaded passageway 32 extending from one end portion thereof, the threaded passageway 32 terminating and communicating with a substantially square recessed portion 34 as best shown in FIG. 3. The recessed cavity or depression 34 can be milled or otherwise formed and extends from adjacent the opposite end portion of the member 30 as best shown in FIG. 1. The threaded passageway 32 is sized, shaped and threaded to correspond to the threaded portion 18 associated the posterior member 12 such that the nut member 32 can be threadedly engaged with the member 12. The passageway 32 and the cavity 34 form a continuous opening through the member 30 for receiving the member 12 and the cavity 34 is, in essence, an expanded portion of the passageway 32. The cavity or depression 34 is also sized and shaped so as to cooperatively receive a correspondingly shaped end portion associated with the handle member 38 as will be hereinafter explained. When the posterior member 12 is insertably received within the anterior member 22, the nut member 30 will be used to generate relative movement between the members 12 and 22 so as to perform a vertebral displacement reduction as will be likewise hereinafter explained. In this regard, like the anterior member 22, the nut member 30 may have at least a portion of its outer surface knurled such as the knurled portion 36 illustrated in FIG. 1 to facilitate the threading of the member 30 onto the posterior member 12 during a surgical procedure.

The handle member 38 includes a substantially elongated tubular portion 40 having a passageway 42 extending therethrough as best shown in FIG. 1. The handle member 38 likewise includes a pair of members 44A and 44B which are positioned substantially perpendicular to the longitudinal axis of the tubular portion 40 at an intermediate location therealong. The members 44A and 44B can be threaded into the tubular portion 40 or can be integrally formed therewith and such members form the T-section of the handle member and facilitate rotation of the handle member 38 by a surgeon during use. One end portion of the tubular handle portion 40 such as the end portion 46 is sized and shaped so as to cooperatively engage the correspondingly shaped cavity or depression 34 associated with the nut member 30. When the handle end portion 46 is engaged with the depression 34, the handle member 38 can be used to threadedly rotate and axially move the member 30 along the threaded portion 18 of the posterior member 12. In this regard, the handle member 38 and the passageway 42 are sized and shaped to slide over the threaded portion 18 of the posterior member 12 so as to engage the nut member 30 as best shown in FIG. 5. Although the handle end portion 46 and the cavity or depression 34 are shown as being substantially square in shape, it is recognized and anticipated that other corresponding shapes could likewise be utilized to accomplish this engagement. Also, importantly, it is recognized and anticipated that other cooperatively engageable means associated with the members 30 and 38 could likewise be utilized to threadedly move the nut member 30 along the threaded portion 18 of member 12.

The opposite end portion of the tubular handle portion 40 likewise includes an opening or depression 48 as best shown in FIGS. 1 and 4, which depression 40 is sized and shaped to correspondingly receive the end portion 16 associated with posterior member 12. Here again, although the opening 48 and the posterior member end portion 16 are shown as being substantially square in shape, it is recognized and anticipated that any correspondingly compatible shapes may be utilized for engaging the end portion 16 with the opening or depression 48 so long as rotational movement of the handle member 38 will cause rotational movement of the posterior member 12 when end portion 16 is engaged with opening 48. Also, importantly, as with the cooperative engagement between handle end portion 46 and cavity 34, it is also recognized and anticipated that other cooperatively engageable means can be utilized to engage the opposite end portion 48 of handle member 38 with the end portion 16 of posterior member 12. Handle member 38, when engaged with the posterior member end portion 16, is used to rotatably position the foot portion 14 in proper position for accomplishing the vertebral displacement reduction between two adjacent vertebrae when the member 12 is insertably positioned between the opposing vertebrae. The handle member 38 can likewise be utilized to reposition the foot portion 14 during a surgical procedure if the foot portion 14 slides out of the proper position or otherwise becomes mislocated or mispositioned during a surgical procedure.

Figure 6:
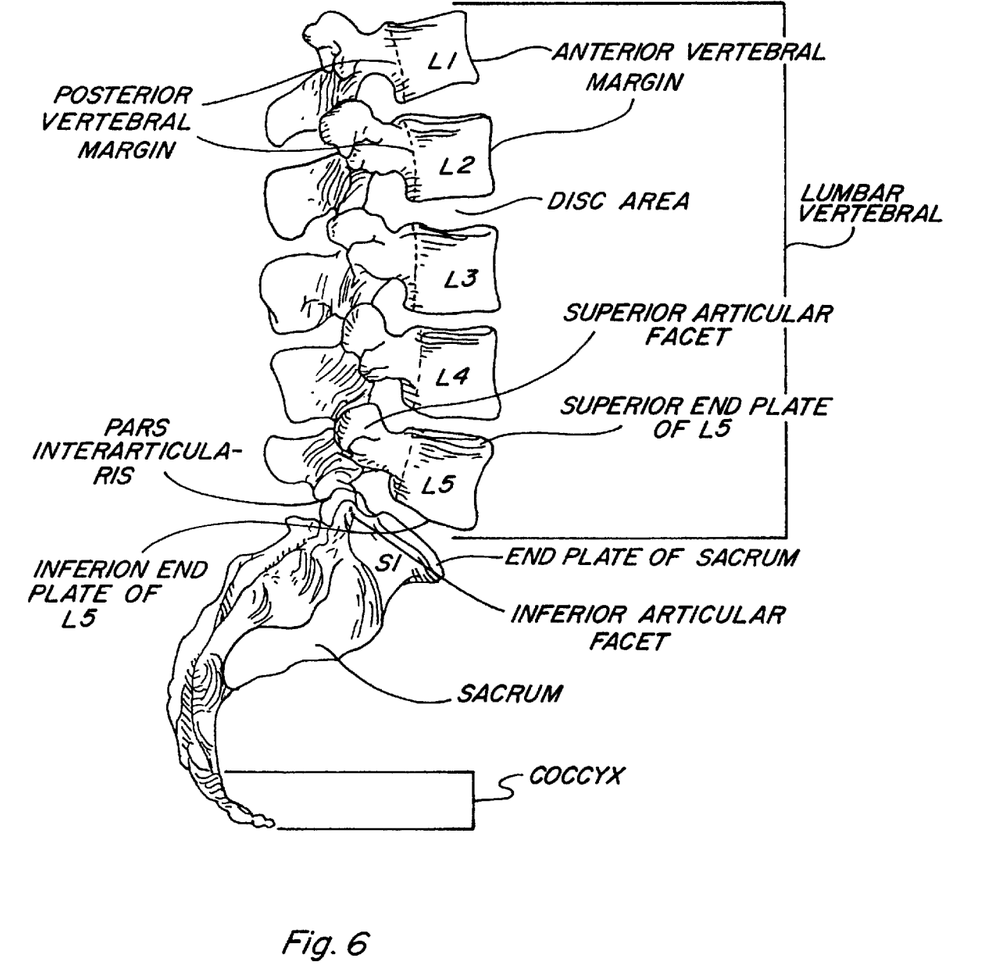
FIG. 6 is a side elevational view of the lumbar vertebrae and sacrum of a normal human spinal column.

FIG. 6 illustrates a normal lumbar and sacrum vertebral column wherein various portions of such vertebral column are identified including the pars interarticularis, the superior articular facet, the inferior articular facet, the anterior vertebral margin of a particular vertebra, the posterior vertebral margin of a particular vertebra, the superior and inferior end plates associated with a particular vertebra, and the disc area located between adjacent vertebrae. In this regard, the disc cartilage is not shown between the respective vertebral members.

Figure 7:
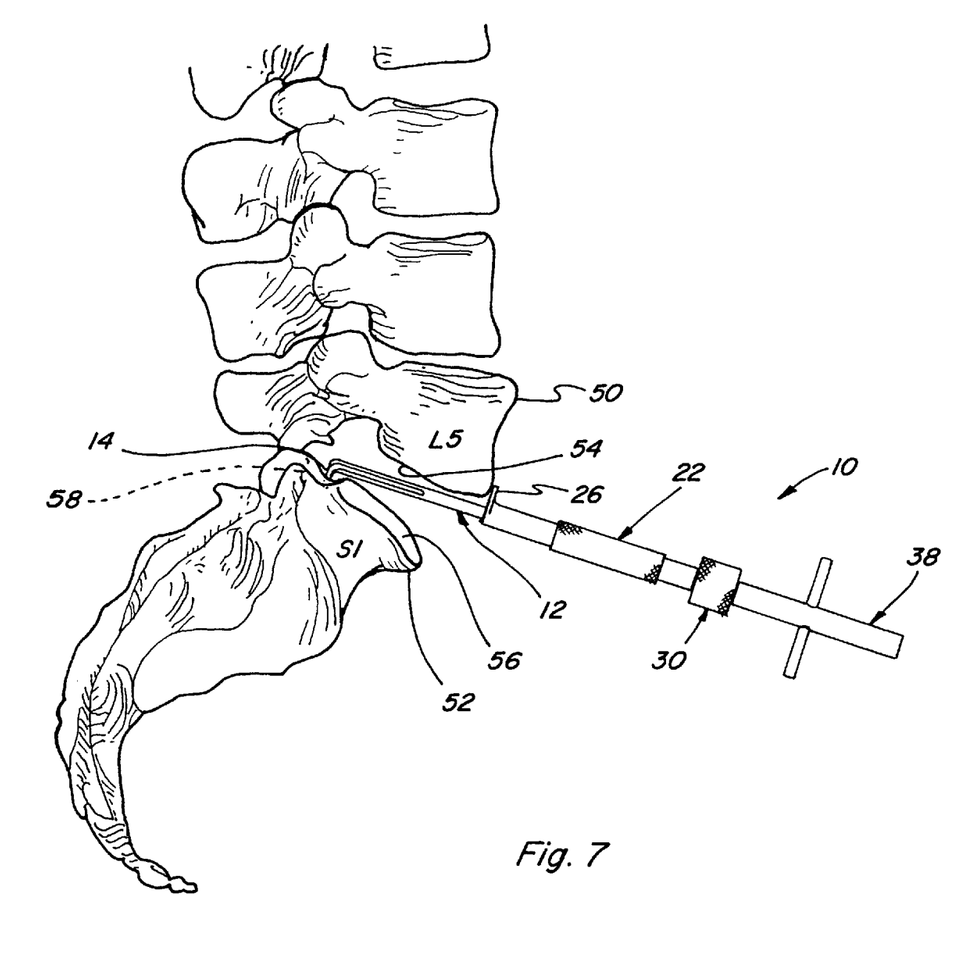
FIG. 7 is a side elevational view of a typical vertebral displacement between the fifth lumbar vertebra and the first sacral vertebra of a human spinal column and showing use of the present surgical tool for reducing such vertebral displacement.

Referring now to FIG. 7, the present tool is shown in use for reducing a vertebral displacement between the fifth lumbar vertebra (L5) and the first sacral vertebra (S1). In FIG. 7, the fifth lumbar vertebra (L5) 50 is shown as having shifted forwardly or anteriorally with respect to the first sacral vertebra (S1) 52 thereby leaving the fifth lumbar vertebra 50 out of alignment with respect to the first sacral vertebra 52. To correct this vertebral displacement, surgery is performed and the present tool 10 is used in the following manner. The spine of a patient is exposed via a standard anterior abdominal surgical approach. The vertebral segments to be treated such as the vertebrae 50 and 52 illustrated in FIG. 7 are defined by lateral x-ray imagining. The interposed intervertebral disc (not shown) is then excised through a window fashioned in the anterior intervertebral disc surface. The opposing vertebral end plates 54 and 56 are then prepared for fusion. The posterior component of the intervertebral disc is opened so as to expose the posteriorly positioned vertebral margin 58.

As illustrated in FIG. 7,. the posterior member 12 of the present tool 10 is separately inserted into the space between the opposing vertebrae 50 and 52, that is, between the empty disc space. When properly positioned, the posterior compression member 12 should lie in the sagittal plane in the mid-line. The opening or depression 48 associated with handle member 38 is then engaged with the end portion 16 of member 12 and, using the handle member 38, the foot portion 14 of the posterior member 12 is then rotated into its proper position so as to engage the posterior vertebral margin 58 of the first sacral vertebra (S1) 52. Once foot portion 14 is properly positioned, the handle member 38 is disengaged from end portion 16 of member 12, and the anterior compression member 26 is then slidably positioned over the posterior member 12 as previously explained. When so positioned, the anterior member 22 is rotated such that its foot portion 26 is positioned over the edge of the anterior vertebral margin of the anteriorly displaced vertebra (L5) 50 as shown in FIG. 7.

Once the anterior member 22 is properly positioned, the compression nut member 30 is threadedly engaged with the threadedly portion 18 of the posterior member 12 such that the cavity or depression 34 is facing outwardly towards the surgeon. The handle end portion 46 is then engaged with the nut depression 34 and the handle member 38 is used to tighten the nut member 30 against the anterior member 22. Continued rotation of the handle member 38 will cause relative movement between the members 12 and 22 and will cause the foot portion 26 to push against the anterior vertebral margin of the fifth lumbar vertebra (L5) 50 thereby pushing such vertebra back into its proper orientation and reducing the vertebral displacement between vertebrae 50 and 52. Should the foot portion 14 of posterior member 12 become disengaged or otherwise dislocated from the posterior vertebral margin 58 of the first sacral vertebra (S1) 52 during the reduction process, the foot portion 14 can be repositioned into its proper position by disengaging the handle member 38 from the nut member 30, reversing the orientation of the handle member 38, and thereafter engaging the handle depression or opening 48 with the end portion 16 of member 12. By referring to the indexed recess 20 associated with end portion 16, the foot portion 14 can be easily repositioned and maneuvered back into proper position by simply rotating the handle member 38 in the proper direction. Once foot portion 14 has been properly repositioned, the handle member 38 can be reengaged with the nut member 30 as shown in FIG. 7 so as to continue the reduction process. Maintaining the respective foot portions 14 and 26 in proper position and engagement with the respective vertebral bodies is important to accomplish a reduction of the vertebral displacement as the relative movement between the members 12 and 22 causes the foot portions 14 and 26 to move toward each other during the reduction process.

Following reduction of the vertebral displacement and confirmation of such reduction by lateral x-ray imaging, the various components of the present tool 10 are removed in reverse order as described above and interbody fusion is then performed using any of the known standard surgical techniques. Once a particular surgical procedure is completed, the various components of the present tool 10 can be cleaned and sterilized using standard techniques and the tool can be readied for use in another surgical application. Although FIG. 7 illustrates use of the present tool 10 with respect to a vertebral displacement between the fifth lumbar vertebra (L5) and the first sacral vertebra (S1), it is recognized and anticipated that the present tool can likewise be utilized to reduce vertebral displacement between any adjacent lumbar vertebrae. Other uses and applications of the present tool 10 are likewise envisioned and anticipated.

It is also recognized that under certain vertebral displacement configurations reduction can be accomplished by positioning the foot portions 14 and 26 in reverse order relative to the adjacent displaced vertebrae. In this situation, foot portion 14 would be engaged with the posterior vertebral margin of the superior vertebral body such as the posterior vertebral margin of vertebra 50 illustrated in FIG. 7, whereas the foot portion 26 would be engaged with the anterior vertebral margin of the inferior vertebral body such as the anterior vertebral margin of vertebra 52 illustrated in FIG. 7. In all other respects, the various components of the present tool 10 would function and operate as previously explained.

A Typical Tool Embodiment

A typical tool 10 constructed in accordance with the teachings of the present invention could be sized and shaped as follows. The posterior compression member 12 could be comprised of a 0.25 inch partially-threaded rod wherein the foot portion 14 would be approximately 0.07 inches thick with rounded edges and would have an exposed footprint of approximately 0.68 inches×0.2 inches. The end portion 16 of member 12 can be milled or otherwise formed to a 0.125 inch square for mating with a similarly configured recess 48 associated with handle member 38. The overall component length of member 12 would be approximately 9.0 inches, the member being partially threaded for approximately 3.75 inches of its overall length. The anterior compression member 22 can be formed from a tubular member having an outside diameter of approximately 0.5 inches and an inside diameter of approximately 0.24 inches. The foot portion 26 would be approximately 0.07 inches thick with rounded edges and would have an exposed footprint of approximately 0.95 inches×0.4 inches. The overall length of member 22 would be approximately 4.5 inches.

The compression nut member 30 can be a cylindrical nut measuring approximately 1.0 inches×0.75 inches with a knurled circumferential surface. The opposed end portions of the member 30 would be polished and the depression 34 would be approximately 0.4 inches square and would be milled to a depth of approximately 0.25 inches. The depression 34 cooperatively receives and accepts a corresponding milled end portion 46 associated with handle member 38. The nut member 30 would be tapped and threaded to correspond to the threads associated with the posterior member 12.

The handle member 38 can be comprised of a polished tubular member having an outside diameter of approximately 0.5 inches and an inside diameter of approximately 0.25 inches. These dimensions define a passageway 24 which would allow the handle member 38 to slide over the threaded portion 18 of the posterior member 12 as dimensioned above. The handle end portion 46 can be milled to a 0.375 inch square so as to cooperatively engage the depression 34 of nut member 30. The opposed end portion of the tubular portion 40 can be taper drilled approximately 0.125 inches terminating in a 0.125 inch square depression 48 which would correspond to and cooperatively receive the 0.125 inch squared end portion 16 associated with the posterior member 12. The two handle portions 44A and 44B would be approximately 1.0 inches×0.25 inches and can be threaded into the tubular portion 40 in opposed relationship to each other at a point equally distant from the opposed end portions of the tubular portion 40. The overall length of the handle member would be approximately 3.875 inches.

All of the above-identified components of the present tool 10 can be made from 304 stainless steel and all of the specific sizes and shapes identified above with respect to a typical tool represent one embodiment of a fully operational tool. It is recognized and anticipated that the specific sizes and shapes of the various components of the present tool 10 can be varied depending upon the particular application without departing from the sprit and scope of the present invention. Other variations and configurations are envisioned and anticipated. The present tool 10 therefore represents an improved method for performing intervertebral displacement reduction, which tool is easy to use and manipulate during a surgical procedure and which tool permits vertebral displacement reduction via an anterior or intra-abdominal approach.

As is evidenced from the foregoing description, certain aspects of the present invention are not limited to the particular details of the examples illustrated herein, and it is therefore contemplated that other modifications, variations, and other uses and applications of the present invention will become apparent to those skilled in the art after considering this specification and the accompanying drawings. All such changes, modifications, variations and other uses and applications which do not depart from the spirit and scope of the invention are deemed to be covered by the invention and are intended to fall within the scope of the following claims.

Other aspects, objects and advantages of the present invention can be obtained from a study of the drawings, the disclosure and the amended claims.

What is claimed is:

1. Apparatus for reducing vertebral displacement between adjacent vertebrae comprising:

a first elongated member having a flange portion associated with one end portion thereof for selectively engaging one of the adjacent vertebrae, the opposite end portion of said first member including threaded means extending along at least a portion of the overall length of said member;

a second elongated tubular member having a passageway extending therethrough adaptable for receiving at least a portion of said first member, said second member being slidably positionable over said first member and being rotatable thereabout, said second member having a flange portion associated with one end portion thereof for selectively engaging the other of the adjacent vertebrae;

a third member having opposed end portions and a passageway extending therethrough, said passageway being at least partially threaded for engaging the threaded means associated with said first member; and a handle member having a passageway extending at least partially therethrough, one end portion of said handle member including means for cooperatively engaging one end portion of said third member such that rotation of said handle member when engaged with said third member will cause rotation of said third member along the threaded means of said first member.

2. The apparatus, as set forth in claim 1, wherein the flange portion associated with the one end portion of said first member is positioned so as to be substantially perpendicular to the longitudinal axis of said first member, said flange portion extending beyond the periphery of said first member on one side portion thereof.

3. The apparatus, as set forth in claim 1, wherein the flange portion associated with the one end portion of said first member is substantially planar.

4. The apparatus, as set forth in claim 1, wherein the flange portion associated with the one end portion of said second member is positioned so as to be substantially perpendicular to the longitudinal axis of said second member, said flange portion extending beyond the periphery of said second member on one side portion thereof.

5. The apparatus, as set forth in claim 1, wherein the flange portion associated with the one end portion of said second member is substantially planar.

6. The apparatus, as set forth in claim 1, wherein said second member includes a knurled portion.

7. The apparatus, as set forth in claim 1, wherein said third member includes a knurled portion.

8. The apparatus, as set forth in claim 1, wherein one end portion of said third member includes a recess cavity which communicates with said passageway, said means associated with the one end portion of said handle member being cooperatively engageable with said recessed cavity.

9. The apparatus, as set forth in claim 1, wherein the opposite end portion of said handle member includes means which are cooperatively engageable with the opposite end portion of said first member such that rotation of said handle member when engaged with said first member will cause rotation of the flange portion associated with said first member.

10. A surgical tool for performing a vertebral displacement reduction between adjacent vertebrae comprising:

a first elongated member having opposed end portions, one end portion of said first member having a foot portion extending therefrom for selectively engaging one of the adjacent vertebrae, said foot portion being oriented at approximately 90° to the longitudinal axis of said first member, said first member further including a threaded portion extending from adjacent the opposite end portion thereof along at least a portion of the overall length of said first member;

a second elongated tubular member having a passageway extending therethrough from end-to-end, said passageway being adaptable for slidably receiving at least a portion of said first member, said second member having a foot portion extending from one end portion thereof for selectively engaging the other of the adjacent vertebrae, said foot portion being oriented at approximately 90° to the longitudinal axis of said second member and being rotatable about said first member when said first member is slidably positioned within said passageway;

a third member having opposed end portions and a passageway extending at least partially therethrough from one end portion thereof, the opposite end portion of said third member including a recessed portion communicating with said passageway, said passageway being at least partially threaded for engaging the threaded portion of said first member; and a handle member having a passageway extending at least partially therethrough, one end portion of said handle member being shaped and dimensioned for cooperatively engaging the recessed portion of said third member such that rotation of said handle member when engaged with said third member will cause rotation of said third member along the threaded portion of said first member.

11. The surgical tool, as set forth in claim 10, wherein the recessed portion of said third member is substantially square in shape.

12. The surgical tool, as set forth in claim 10, wherein the opposite end portion of said first member includes an indexing mark for determining the position of the flange portion relative thereto.

13. The surgical tool, as set forth in claim 10, wherein the opposite end portion of said handle member includes means for cooperatively engaging the opposite end portion of said first member such that rotation of said handle member when engaged with said first member will cause rotation of the foot portion associated with said first member.

14. The surgical tool, as set forth in claim 10, wherein the opposite end portion of said first member includes a substantially square terminal end portion, said means associated with the opposite end portion of said handle member including an opening which is sized and shaped to correspondingly receive the squared terminal end portion of said first member.

15. The surgical tool, as set forth in claim 10, wherein said handle member includes a pair of members which are positioned substantially perpendicular to the longitudinal axis of said handle member in opposed relationship to each other at an intermediate location therealong.

16. Apparatus for aligning adjacent vertebrae when inserted therebetween comprising:

a first elongated member having opposed end portions, a substantially planar foot portion associated with one end portion of said first member for selectively engaging one of the adjacent vertebrae, said foot portion being oriented at approximately 90° to the longitudinal axis of said first member, the opposite end portion of said first member including a substantially square terminal end portion, and threaded means extending from said substantially square terminal end portion along at least a portion of the overall length of said first member;

a second elongated tubular member having a passageway extending therethrough adaptable for receiving at least a portion of said first member, said second member being slidably positionable over said first member and being rotatable thereabout, said second member having a substantially planar foot portion associated with one end portion thereof for selectively engaging the other of the adjacent vertebrae, said foot portion being oriented at approximately 90° to the longitudinal axis of said second member;

a cylindrical nut member having opposed end portions and a passageway extending therethrough from end-to-end, one end portion of said passageway being expanded adjacent one end portion of said nut member, at least a portion of said passageway being correspondingly threaded for engaging the threaded means associated with said first member; and a handle member having a passageway extending at least partially therethrough, one end portion of said handle member being sized and shaped so as to cooperatively engage the expanded portion of the passageway associated with said cylindrical nut member such that rotation of said handle member will cause rotation of said nut member along the threaded means of said first member, the opposite end portion of said handle member including a substantially square opening adaptable for cooperatively receiving the substantially square terminal end portion of said first member such that rotation of said handle member will cause rotation of the foot portion associate with said first member, said handle member further including a pair of opposed members positioned substantially perpendicular to the longitudinal axis of said handle member at an intermediate location along its length for facilitating the gripping and rotation of the said handle member by a user.

17. A method for reducing vertebral displacement between adjacent vertebrae comprising:

providing a first elongated member having a flange portion associated with one end portion thereof for selectively engaging one of the adjacent vertebrae, the opposite end portion of said first member including a threaded portion extending along at least a portion of the overall length of said first member;

inserting said first elongated member between the adjacent vertebrae;

rotating said first elongated member such that said flange portion engages the posterior vertebral margin of one of the adjacent vertebrae;

providing a second elongated tubular member having a passageway extending therethrough adaptable for receiving at least a portion of said first member, said second member being slidably positionable over said first member and being rotatable thereabout, said second member having a flange portion associated with at least one end portion thereof for selectively engaging the other of the adjacent vertebrae;

slidably positioning said second elongated member over said first elongated member and rotating said second member such that its flange portion is positioned over the edge of the anterior vertebral margin of the other of the adjacent vertebrae;

providing a third member having opposed end portions and a passageway extending therethrough, said passageway being at least partially threaded for engaging the threaded portion of said first member;

threading said third member onto the threaded portion of said first member;

providing a handle member having a passageway extending at least partially therethrough, one end portion of said handle member including means for cooperatively engaging one end portion of said third member;

engaging the handle member with said third member and rotating said handle member so as to move said third member along the threaded portion of said first member until said third member engages said second member; and continuing the rotation of said handle member so as to further tighten said third member against said second member to perform the reduction of the vertebral displacement between the adjacent vertebrae.

18. The method, as set forth in claim 17, wherein the opposite end portion of said handle member includes means for engaging the opposite end portion of said first member, said handle member being utilized to rotate said first member such that its flange portion engages the posterior vertebral margin of one of the adjacent vertebrae.

19. A method for reducing vertebral displacement between adjacent vertebrae comprising:

providing a first elongated member having opposed end portions, one end portion of said first member having a foot portion extending therefrom for selectively engaging one of the adjacent vertebrae, said foot portion being oriented at approximately 90° to the longitudinal axis of said first member, said first member further including a threaded portion extending from adjacent the opposite end portion thereof along at least a portion of the overall length of said first member;

providing a second elongated tubular member having a passageway extending therethrough from end-to-end, said passageway being adaptable for slidably receiving at least a portion of said first member, said second member having a foot portion extending from one end portion thereof for selectively engaging the other of the adjacent vertebrae, said foot portion being oriented at approximately 90° to the longitudinal axis of said second member and being rotatable about said first member when said first member is slidably positioned within said passageway;

providing a third member having opposed end portions and a passageway extending at least partially therethrough from one end portion thereof, the opposite end portion of said third member including a recessed portion communicating with said passageway, said passageway being at least partially threaded for engaging the threaded portion of said first member;

providing a handle member having a passageway extending at least partially therethrough, one end portion of said handle member being shaped and dimensioned for cooperatively engaging the recessed portion of said third member such that rotation of said handle member when engaged with said third member will cause rotation of said third member along the threaded portion of said first member, the opposite end portion of said handle member being shaped and dimensioned for cooperatively engaging the opposite end portion of said first member such that rotation of said handle member when engaged with said first member will cause rotation of the foot portion associated with said first member;

inserting said first elongated member between the adjacent vertebrae;

engaging the opposite end portion of said handle member with the opposite end portion of said first member and rotating said handle member such that the foot portion of said first member engages the posterior vertebral margin of one of the adjacent vertebrae;

disengaging said handle member from the opposite end portion of said first member;

slidably positioning said second elongated member over said first elongated member and rotating said second member such that its foot portion is positioned over the edge of the anterior vertebral margin of the other of the adjacent vertebrae;

threading said third member onto the threaded portion of said first member;

engaging the one end portion of said handle member with the recessed portion of said third member and rotating said handle member so as to move said third member into engagement with said second member; and continuing the rotation of said handle member so as to tighten said third member against said second member which in turn pushes against the anterior vertebral margin of the other of the adjacent vertebrae, the continued rotation of said handle member performing a vertebral displacement reduction between the adjacent vertebrae.

* * * * *

UNITED STATES PATENT AND TRADEMARK OFFICE
CERTIFICATE OF CORRECTION

PATENT NO. : 6,159,212
DATED : December 12, 2000
INVENTOR(S) : Schoedinger et al     It is certified that errors appear in the above-identified patent and that said Letters Patent are hereby corrected as shown below:

In the BACKGROUND ART:
Col. 1, line 33, delete "common is" and insert --common in --.
Col. 1, line 49, delete "develop" and insert -- developed --.

In the SUMMARY OF THE INVENTION:
Col. 2, line 19, delete "orientated" and insert -- oriented --.
Col. 2, line 41, delete "is" and insert -- in --.
Col. 2, line 52, delete "cooperative" and insert -- cooperatively --.

In the DETAILED DESCRIPTION OF THE INVENTION:
Col. 4, line 54, delete "position" and insert -- positioned --.
Col. 5, line 2, delete "associated" and insert -- associated with --.
Col. 6, line 61, delete "threadedly" and insert -- threaded --.
Col. 8, line 2, please add a new paragraph before the words "The anterior".
Col. 8, line 46, delete "sprit" and insert -- spirit --.

In the claims:
Claim 16, Col. 11, line 33, delete "associate" and insert -- associated --.

Signed and Sealed this

Eighth Day of May, 2001

*Attest:*

NICHOLAS P. GODICI

*Attesting Officer*      Acting Director of the United States Patent and Trademark Office